(12) United States Patent
Koch

(10) Patent No.: US 7,641,748 B2
(45) Date of Patent: Jan. 5, 2010

(54) HIGHLY ENERGY-PRODUCING COMPOUND

(75) Inventor: Ernst-Christian Koch, Kaiserslautern (DE)

(73) Assignee: Diehl BGT Defence GmbH & Co., KG, Ueberlingen (DE)

( * ) Notice: Subject to any disclaimer, the term of this patent is extended or adjusted under 35 U.S.C. 154(b) by 318 days.

(21) Appl. No.: 11/526,129

(22) Filed: Sep. 22, 2006

(65) Prior Publication Data

US 2009/0299106 A1      Dec. 3, 2009

(30) Foreign Application Priority Data

Sep. 23, 2005    (DE) .................. 10 2005 045 419

(51) Int. Cl.
*C06B 25/00*    (2006.01)

(52) U.S. Cl. ....................................................... 149/88

(58) Field of Classification Search .................... 149/88
See application file for complete search history.

(56) References Cited

U.S. PATENT DOCUMENTS 6,340,780 B1    1/2002   Latypov et al.

OTHER PUBLICATIONS

Lebedev et al. CAS Acession No. 1998:498840.*

* cited by examiner

*Primary Examiner*—Rei-Tsang Shiao
*Assistant Examiner*—Joseph R Kosack
(74) *Attorney, Agent, or Firm*—Scully, Scott, Murphy & Presser, P.C.

(57) ABSTRACT

A highly energy-producing compound which can be used, for example, as an explosive, propellant, oxidant and the like, and which includes an alkyne unit in which at least one hydrogen atom has been replaced by a trinitromethyl-$C(NO_2)_3$ group.

2 Claims, No Drawings

HIGHLY ENERGY-PRODUCING COMPOUND

BACKGROUND OF THE INVENTION

1. Field of the Invention

The present invention relates to a novel highly energy-producing compound, which can advantageously be used, for example, as explosive, propellant, oxidant and the like.

Among the uniform energy-producing materials for use as explosives and propellants, nitrocarbons of the general composition $C_n(NO_2)_m$ are of particular interest. Nitrocarbons can, depending on the degree of hybridization of the carbon, be divided into permitroalkanes, pernitroalkenes, pernitroaromatics and pernitroacetylenes. The group of homoleptic nitrocarbon compounds encompasses, to the present date, tetranitromethane $C(NO_2)_4$, hexanitroethane $C_2(NO_2)_6$, tetranitroethylene $C_2(NO_2)_4$, hexanitrobenzene $C_6(NO_2)_6$, decanitrobiphenyl $C_{12}(NO_2)_{10}$ and the recently synthesized octanitrocubane $C_8(NO_2)_8$.

In the case of the linear alkanes, calculations have shown that the strong van der Waals forces in molecules such as octanitropropane and decanitrobutane lead to considerable destabilization of the C—N bond, so that these substances are certainly not stable. The slow decomposition of hexanitroethane (hereinafter referred to as HNE for short) at as low as 50° C. also shows that even more rapid decomposition can be expected in the case of higher homologues.

SUMMARY OF THE INVENTION

It is an object of the present invention to provide a highly energy-producing and at the same time sufficiently stable compound.

The novel highly energy-producing compound of the invention comprises an alkyne unit in which at least one hydrogen atom has been replaced by a trinitromethyl group. In such a compound, the trinitromethyl groups are separated sufficiently far by the alkyne unit for no C—N bond weakening, which promotes thermal decomposition to exist.

In an advantageous development, at least one further hydrogen atom of the alkyne unit is replaced by a radical selected from the group consisting of $NO_2$, NO, $NH_2$, $N(NO_2)_2$ and alkyl.

The highly energy-producing compound is preferably a trinitromethylacetylene derivative of the formula R—C≡C—C($NO_2$)$_3$, where R is selected from the group consisting of H, $NO_2$, NO, $NH_2$, $N(NO_2)_2$, $C(NO_2)_3$ and alkyl, and in particular bis(trinitromethyl)acetylene $C_4(NO_2)_6$ for R=C($NO_2$)$_3$, or a trinitromethylbutadiyne derivative of the formula R—C≡C—C≡C—C($NO_2$)$_3$, where R is selected from the group consisting of H, $NO_2$, NO, $NH_2$, $N(NO_2)_2$, $C(NO_2)_3$ and alkyl, and in particular bis(trinitromethyl)butadiyne $C_6H_2(NO_2)_6$.

Furthermore, a carbocyclic skeleton, for example tetrahedrane, [3]-prismane and cubane, can be built up using the above highly energy-producing compounds of the invention.

A highly energy-producing compound according to the invention can, for example, be prepared by reacting a mono (trialkylsilyl)- or bis(trialkylsilyl)-substituted alkyne with a halotrinitromethane, by reacting a metal nitroformate with a monohaloacetylene or dihalo-acetylene or by reacting a nitronium compound with a tris(trialkylsilyl)- or hexakis(trialkylsilyl)-substituted alkyne.

The highly energy-producing compound of the invention is particularly suitable as explosive, propellant, oxidant and the like.

DETAILED DESCRIPTION OF EXEMPLARY EMBODIMENTS OF THE INVENTION

The abovementioned and also further features and advantages of the invention will be more readily understood from the following description of a preferred, nonlimiting example of a compound according to the invention.

Particularly suitable and practicable compounds for the purposes of the invention have been found to be:
  a)—trinitromethylacetylene derivatives of the formula R—C≡C—C($NO_2$)$_3$,
      where R is selected from the group consisting of H, $NO_2$, NO, $NH_2$, $N(NO_2)_2$, $C(NO_2)_3$ and alkyl,
  b)—trinitromethylbutadiyne derivatives of the formula R—C≡C—C≡C—C($NO_2$)$_3$,
      where R is selected from the group consisting of H, $NO_2$, NO, $NH_2$, $N(NO_2)_2$, $C(NO_2)_3$ and alkyl.

For a), bis(trinitromethyl)acetylene (hereinafter also referred to as BTNMA for short) $C_4(NO_2)_6$ for R=C($NO_2$)$_3$ is proposed in particular, and for b) bis(trinitromethyl) butadiyne $C_6H_2(NO_2)_6$ for $R^1$=C($NO_2$)$_3$ is proposed in particular.

Semiempirical calculations have shown a higher stability for BTNMA compared to HNE. Thus, the C—N bond lengths in HNE are an average of 2 pm longer than in the case of BTNMA (164.4 pm compared to 162.3 pm). A look at the electrostatic potentials also shows a lower positive charge over the molecule in the case of BTNMA, which, according to Politzer, likewise indicates a higher stability and thus lower sensitivity to shock and friction.

Regardless of this, the enthalpy of formation of BTNMA is, owing to the energy-rich acetylene C2 unit, higher than that of HNE by a factor of 1.7. A further advantage of BTNMA over the other nitrocarbons known hitherto, especially compared to the thermally very sensitive tetranitroethylene, is the generally high reactivity of triple bonds, which can be utilized in the construction of carbon skeletons.

The abovementioned compounds are thus also suitable as starting molecules for, for example, carbocyclic skeletons such as tetrakis(trinitromethyl)tetrahedrane $(C(NO_2)_3)_4$, hexakis(trinitromethyl)-[3]-prismane $(C(NO_2)_3)_6$ or octakis (trinitromethyl)cubane $(C(NO_2)_3)_8$.

To prepare BTNMA, the following synthetic routes are conceivable.
  a) reaction of bis(trimethylsilyl)acetylene with a halotrinitromethane according to, for example, $$(H_3C)_3Si-CC-Si(CH_3)_3 + 2ClC(NO_2)_3 = 2TMS-Cl + BTNMA$$

b) reaction of a metal nitroformate $MC(NO_2)_3$ with a dihaloacetylene prepared in situ, according to, for example, $$2MC(NO_2)_3 + \{C_2Cl_2\} = 2MCl + BTNMA$$

c) reaction of a hexakis(trimethylsilyl)but-2-yne with a nitronium compound according to, for example, $$(TMS)_3C-C≡C-C(TMS)_3 + 6NO_2X = 6TMS-X + BTNMA$$

where X=F, Cl, Br, I, $BF_4$ or any Lewis acid.

Analogous reactions also lead to all other compounds according to the present invention.

What is claimed is:

1. A highly energy-producing compound, wherein the compound is a trinitromethylacetylene derivative of the formula R—C≡C—C(NO$_2$)$_3$ and R is selected from the group consisting of H, NO$_2$, NO, NH$_2$, N(NO$_2$)$_2$, C(NO$_2$)$_3$ and alkyl.

2. A highly energy-producing compound, wherein the compound is a trinitromethylbutadiyne derivative of the formula R—C≡C—C≡C—C(NO$_2$)$_3$ and R is selected from the group consisting of H, NO$_2$, NO, NH$_2$, N(NO$_2$)$_2$, C(NO$_2$)$_3$ and alkyl.

* * * * *